US010520476B2

(12) United States Patent
Furr (10) Patent No.: US 10,520,476 B2
(45) Date of Patent: Dec. 31, 2019

(54) METHOD FOR INSPECTING HIGH DENSITY POLYETHYLENE PIPE

(71) Applicant: Loenbro Inspection, LLC., Black Eagle, MT (US)

(72) Inventor: Parrish Alan Furr, Trussville, AL (US)

(73) Assignee: Loenbro Inspection, LLC, Black Eagle, MT (US)

(*) Notice: Subject to any disclaimer, the term of this patent is extended or adjusted under 35 U.S.C. 154(b) by 161 days.

(21) Appl. No.: 15/202,170

(22) Filed: Jul. 5, 2016

(65) Prior Publication Data

US 2018/0011064 A1    Jan. 11, 2018

(51) Int. Cl.
| | |
|---|---|
| *G01N 29/44* | (2006.01) |
| *G01N 29/30* | (2006.01) |
| *G01N 29/07* | (2006.01) |
| *G01N 29/48* | (2006.01) |
| *G01N 29/26* | (2006.01) |

(52) U.S. Cl.
CPC ......... *G01N 29/4445* (2013.01); *G01N 29/07* (2013.01); *G01N 29/262* (2013.01); *G01N 29/30* (2013.01); *G01N 29/4463* (2013.01); *G01N 29/48* (2013.01); *G01N 2291/2634* (2013.01)

(58) Field of Classification Search
CPC .... G01N 29/4445; G01N 29/07; G01N 29/30; G01N 29/48; G01N 2291/2634
USPC ........................................................ 73/1.86
See application file for complete search history.

(56) References Cited

U.S. PATENT DOCUMENTS

| | | | | |
|---|---|---|---|---|
| 6,415,644 | B1* | 7/2002 | Rockwood | G01B 17/02 73/1.86 |
| 7,617,715 | B2* | 11/2009 | Georgeson | G01N 29/11 29/593 |

FOREIGN PATENT DOCUMENTS

CN    203894199 U    * 10/2014

OTHER PUBLICATIONS

Translation CN 203894199 dated Oct. 2014.*
Plastic Fantastic?—An NDE Inspection Solution for HDPE Butt Welds. David MaClennan, Irene G Pettigrew and Colin R Bird. 18th World Conference on Nondestructive Testing. Durban, South Africa. Apr. 16-20, 2012.*

* cited by examiner

*Primary Examiner* — Natalie Huls
*Assistant Examiner* — Monica S Young
(74) *Attorney, Agent, or Firm* — Haynes and Boone, LLP (57) ABSTRACT

A system and method directed to inspecting a high density polyethylene pipe. The system includes a pipe inspection tool that is positioned about a fused polyethylene pipe joint. The inspection tool may include search units, a pipe carriage, a pulser and a phased array testing instrument programmed to adjust an amplitude response signal from the search units based on a vertically established time corrected gain curve. The inspection tool is rotated around the high density polyethylene pipe joint while propagating acoustical waves at various patterns and angles through the polyethylene pipe joint. Prior to the joint inspection, the inspection tool is calibrated using a calibration tool which includes a block having an array of equal sized bores positioned along different axis' through the block's depth. The block is constructed of the same material type and grade as the pipes that were fused together to form the polyethylene pipe joint.

7 Claims, 8 Drawing Sheets

METHOD FOR INSPECTING HIGH DENSITY POLYETHYLENE PIPE

FIELD OF THE DISCLOSURE

The present disclosure relates generally to pipe inspection, and more specifically, to the inspection of pipe joints. More particularly still, the present disclosure relates to systems and methods for inspecting pipe joint integrity after the fusion of two high density polyethylene pipes.

BACKGROUND

It is common to utilize high density polyethylene (HDPE) piping to convey fluids in a wide spectrum of industries. Compared to more traditional steel pipe, HDPE pipe has a greater ease of installation, lower maintenance requirements and lower leakage rate making it a preferred conveyance medium in the water, energy and nuclear industries over its metallic alloy counterparts.

HDPE pipe sections are commonly joined together using a fusion process such as butt-fusion jointing. This process involves the simultaneous heating of adjacent ends of HDPE pipe sections to be joined until a molten state is attained on the contact surface of each end. The two surfaces are brought together under controlled pressure for a specific cooling time and a homogenous fusion joint is formed. Notwithstanding the foregoing, HDPE joints may have various flaws, such as lack of fusion, cold fusion (partial bond), inclusion (embedded foreign objects), and voids.

Current inspection techniques of HDPE pipe include visual inspection and phased array ultrasonic inspection. Phased array ultrasonic inspection is a technique which involves directing acoustical energy towards an object to determine whether the object contains flaws. HDPE material however, has some specific acoustic characteristics, such as hindering the propagation of shear sound waves, which make butt joint inspection utilizing phased array ultrasonic inspection difficult, particularly when the fusion line is perpendicular to the material surface as is the case with HDPE butt joints. Since the repair of a fused. HDPE pipe joint is typically expensive a need has arisen to optimally test the integrity of fused HDPE pipe joint in a non-destructive manner.

DESCRIPTION OF ILLUSTRATIVE EMBODIMENTS

The disclosure may repeat reference numerals and/or letters in the various examples or figures. This repetition is for the purpose of simplicity and clarity and does not in itself dictate a relationship between the various embodiments and/or configurations discussed. Further, spatially relative terms, such as beneath, below, lower, above, upper, upstream, downstream, and the like, may be used herein for ease of description to describe one element or feature's relationship to another element(s) or feature(s) as illustrated, the upward direction being toward the top of the corresponding figure and the downward direction being toward the bottom of the corresponding figure. Unless otherwise stated, the spatially relative terms are intended to encompass different orientations of the apparatus in use or operation in addition to the orientation depicted in the figures. For example, if an apparatus in the figures is turned over, elements described as being "below" or "beneath" other elements or features would then be oriented "above" the other elements or features. Thus, the exemplary term "below" can encompass both an orientation of above and below. The apparatus may be otherwise oriented (rotated 90 degrees or at other orientations) and the spatially relative descriptors used herein may likewise be interpreted accordingly.

Illustrative embodiments and related methods of the present disclosure are described below as they might be employed in the inspection of high density polyethylene (HDPE) pipe joints. As used herein, HDPE means a polyethylene thermoplastic made from petroleum having a high strength to density ratio. In a generalized embodiment, a pipe inspection tool is positioned about a fused HDPE pipe joint formed between adjacent HDPE pipe sections. Typically the joint is formed in a plane that is perpendicular to the axis of the two fused HDPE pipe sections. The pipe inspection tool includes two search units, a pipe scanner, a pulser-receiver module and a phased array testing instrument. The pipe inspection tool is rotated around the periphery of the HDPE pipe joint while propagating acoustical waves in various patterns and at various angles through the HDPE pipe joint to detect flaws that may have occurred during the HDPE pipe joint fusion process. Prior to the joint inspection, the pipe inspection tool is calibrated using a calibration tool which includes a block having two or more sized holes positioned along different parallel axis' through the depth of the block. The block is constructed of the same material type and grade as the HDPE pipes which were fused together to form a HDPE pipe joint. In some embodiments, the HDPE block is formed to have a material grain that is oriented in the same direction of the HDPE pipe to be inspected once the calibration is complete. Prior to inspection of a particular pipe utilizing the pipe inspection tool, the pipe inspection tool must be specifically calibrated for use with the particular pipe, as described in the calibration process below.

Figure 1:
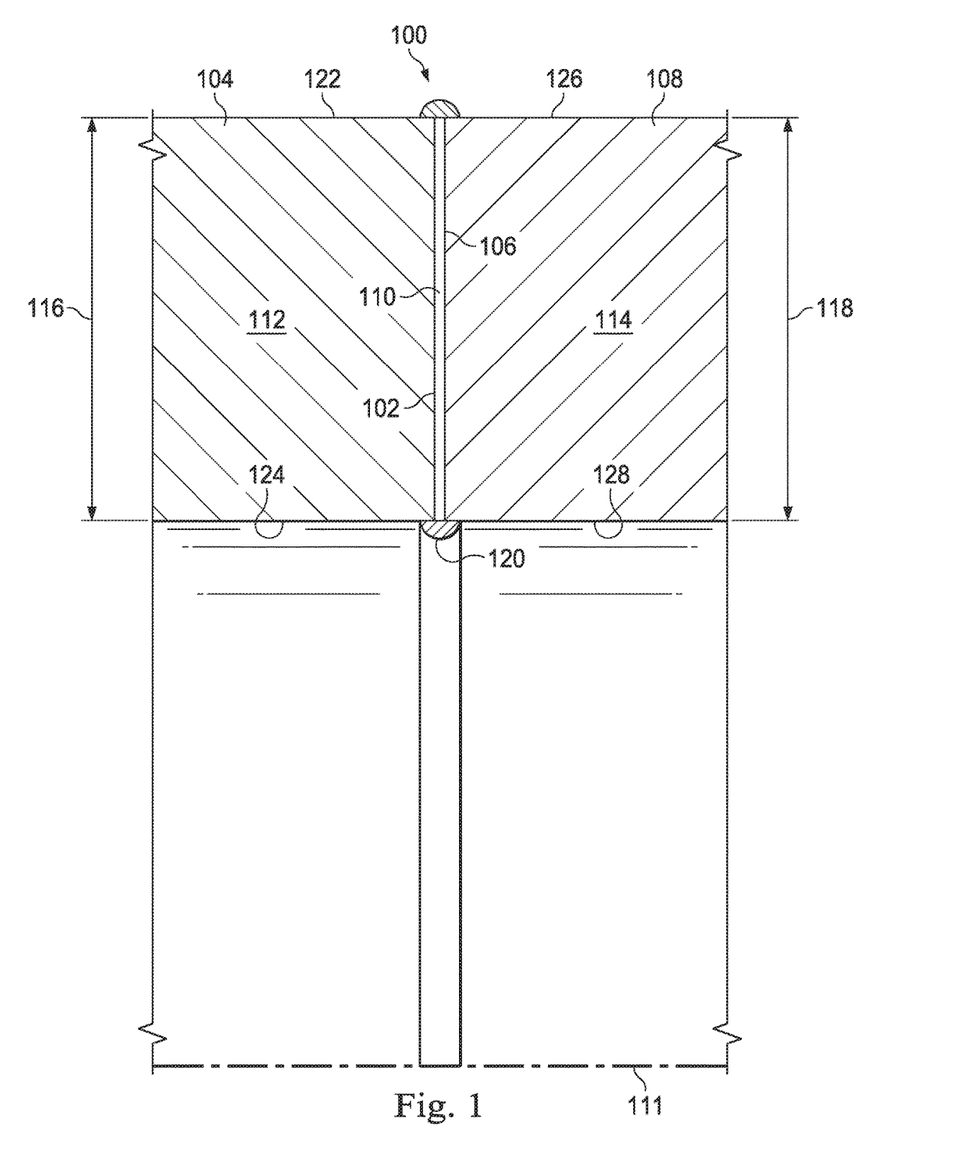
FIG. 1 depicts an enlarged partial sectional view a fused high density polyethylene (HDPE) joint, according to one or more illustrative embodiments.

Referring to FIG. 1 an enlarged partial sectional view a fused HDPE pipe joint 100 is illustrated. The joint 100 is assembled by heating the downstream end 102 of a first HDPE pipe section 104 and the upstream end 106 of a second HDPE pipe section 108 and joining the two ends 102, 106 under controlled pressure for a specific cooling time. A fusion plane 110 perpendicular to the primary axis 111 of the pipe sections 104, 108 and to the material surface of the first HDPE pipe wall 112 and the second HDPE pipe wall 114 is formed between the two ends 102, 106. The fusion plane 110 is formed at the same length as the first HDPE pipe wall thickness 116 and the second HDPE pipe wall thickness 118 respectively. During the cooling process a fusion bead 120 is formed about the fusion plane 110, on the first pipe outside diameter (OD) surface 122 and the second pipe OD surface 126, and also about the fusion plane 110 on the first pipe inside diameter (ID) surface 124 and the second pipe diameter ID surface 128. The fusion bead 120 is normally removed from the pipe joint 100, such as by machining, after a joint integrity test has been performed.

Figure 2:
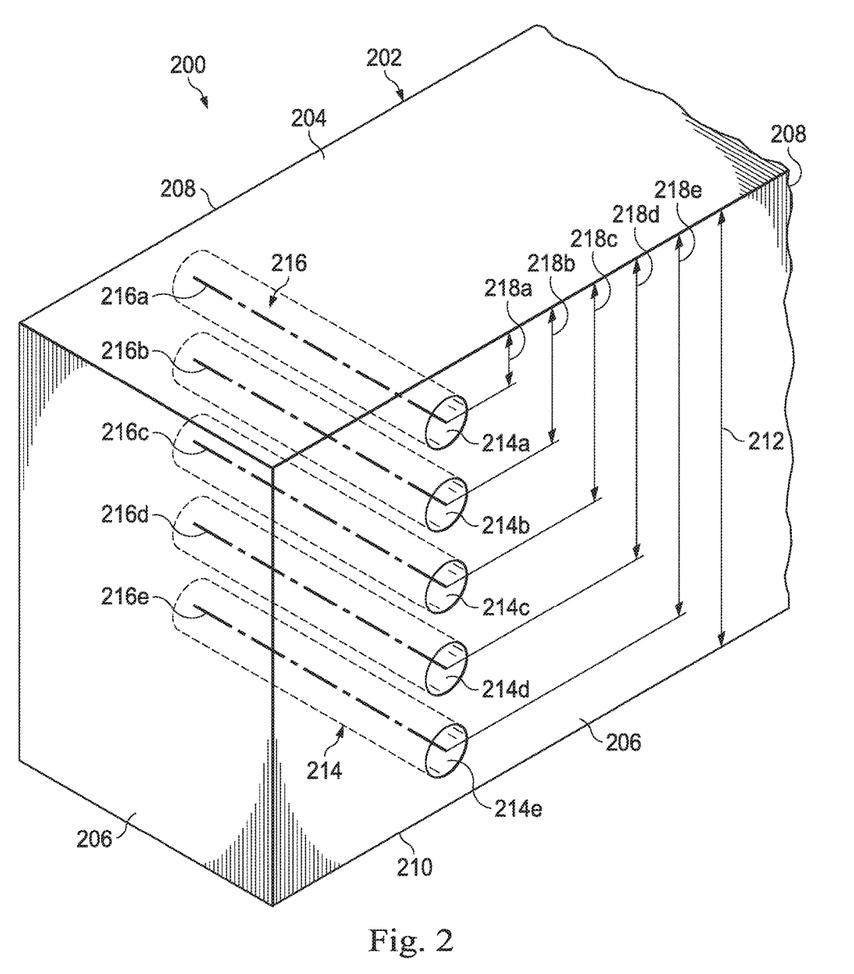
FIG. 2 depicts an enlarged elevation view of a HDPE calibration tool, according to one or more illustrative embodiments.

FIG. 2 illustrates an enlarged elevation view of a HDPE calibration tool 200. The calibration tool includes a HDPE block 202 having at least a first surface 204. Although block 202 is not limited to a particular shape for purposes of the disclosure, in one or more embodiments, block 202 is rectangular and includes a second surface 206, a third surface 208 and a fourth surface 210. In the case of a rectangular block 202, the first surface 204 of the block 202 is oriented to be parallel with the fourth surface 210, while the second surface 206 of the block 202 is oriented to be parallel with the third surface 208. Regardless of the shape of block 202, two or more spaced apart bores 214 are formed in block 202, each bore 214 formed along an axis 216 that is substantially parallel with the first surface 204. In one or more embodiments, a plurality of bores 214 may be formed in block 202, while in other embodiments, at least 5 bores 214 are formed in block 202. In one or more embodiments, bores 214 extend completely through block 202, such as from the second surface 206 to the third surface 208, while in other embodiments one or more bores 214 extend only partially through block 202. In one or more embodiments, bores 214 are of the similar diameter. As will be discussed below, the plurality of bores 214 is used to verify that a select sound pressure to be used in a proposed pipe inspection is adequate and similar throughout the depth 212 of the block 202. In one or more preferred embodiments, the HDPE block 202 is of the same material type and grade as the pipes to be inspected, such as first and second HDPE pipes 104, 108 in the illustrated embodiments. Thus, it is necessary to ascertain the material type and grade of the HDPE pipe to be inspected prior to calibration so that the appropriate calibration block 202 may be selected. Additionally, in preferred embodiments, the HDPE block 202 should have a depth 212 selected to be substantially the same depth as the first HDPE pipe wall thickness 116 and the second HDPE pipe wall thickness 118.

Each bore 214 is formed along a corresponding axis 216 at a known depth relative to the first surface 204 and is oriented parallel to the first surface 204 (and the fourth surface 210 in the case of a rectangular block 202). For instance, the first bore 214a is formed along a first axis 216a at a first depth 218a relative to the first surface 204. Similarly, the second bore 214b is formed along a second axis 216b at a second depth 218b relative to the first surface 204. The third bore 214c is formed along a third axis 216c at a third depth 218c relative to the first surface 204. Additionally, the fourth bore 214d is formed a long a fourth axis 216d at fourth depth 218d relative to the first surface 204. A fifth bore 214e is formed a long a fifth axis 216e at a fifth depth 218e relative to the first surface 204. The pattern of drilling bores through the block 202 as described above may continue for an "N" number of bores. In one or more preferred embodiments, the distance between each bores should not exceed twenty five percent of the block's depth 212.

Figure 2A:
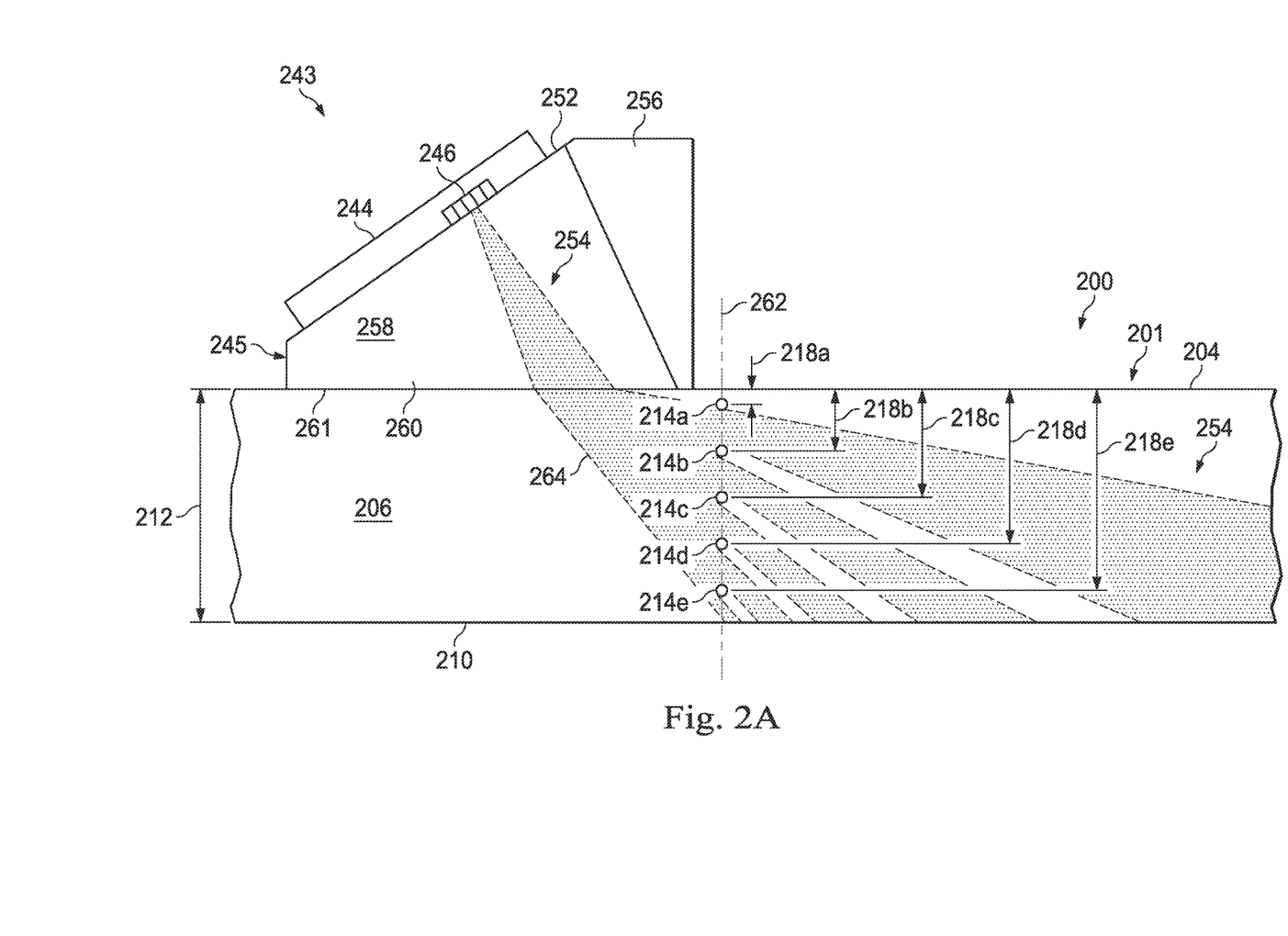
FIG. 2A depicts an elevation view of the initial calibration process setup using the calibration tool and a search unit, according to one or more illustrative embodiments.
Figure 3:
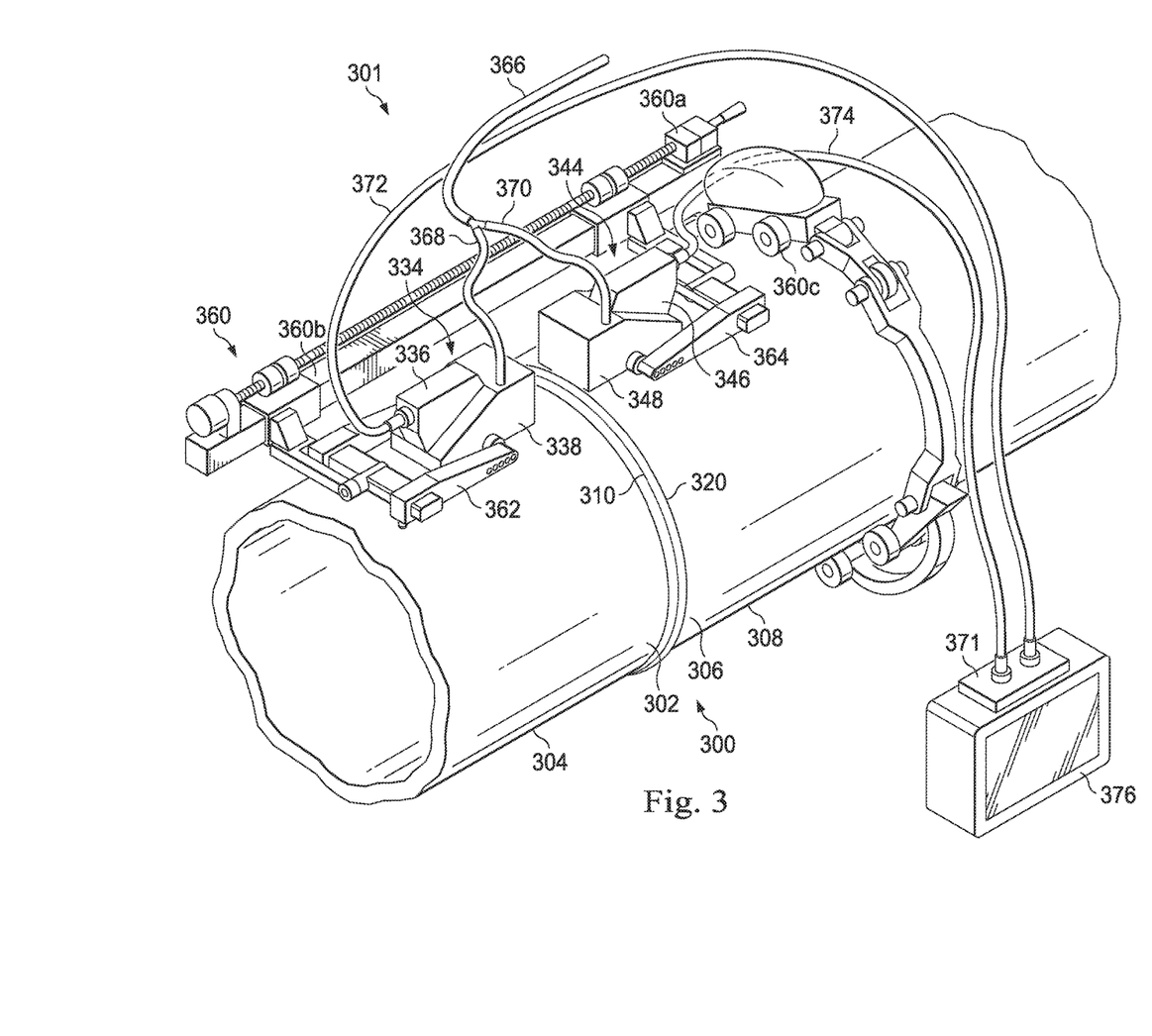
FIG. 3 depicts a perspective view of a HDPE pipe inspection tool situated on top of a fused PE pipe joint.

FIG. 2A illustrates an elevation view of the HDPE calibration tool 200 utilized in initial calibration of a search unit 243 of a pipe inspection tool (see FIG. 3). The search unit 243 includes a transducer 244 and a liquid enclosure 245. The transducer 244 may be any suitable transducer for propagating a longitudinal signal 254, such as a longitudinal sound wave, through the liquid enclosure 245. In one embodiment, transducer 244 may be an Olympus Model 2.25L64-A2 transducer, for example. Likewise, the liquid enclosure 245 may be any enclosure suitable for containing a liquid 258 for controlling the speed of propagation of a transducer signal therethrough. In one embodiment, liquid enclosure 245 may be an Olympus Model ABWX 1663 liquid enclosure, for example. In one or more embodiments, the liquid enclosure 245 may have a wedge shape. The transducer 244 houses transducer elements 246. As illustrated, the liquid enclosure 245 is positioned between the transducer 244 and the HDPE calibration tool 200. In one or more embodiments, transducer 244, and in particular, transducer elements 246, are positioned so as to introduce longitudinal signal 254 into PE block 202 at an acute angle relative to first surface 204 of HDPE block 202. For this reason, liquid enclosure 245 may have a sloped surface 252 relative to the base 260 of liquid enclosure 245 that abuts first surface 204 of HDPE block 202. Additionally, in one or more embodiments the transducer 244 and the liquid enclosure may be coupled. The transducer elements 246 are operable to convert an electric pulse to a longitudinal signal 254 and to convert a returning reflected signal into an electric amplitude signal. Due to the acoustic properties of HDPE, in one or more embodiments, at least 32 elements 246 are provided in the transducer 244. The liquid enclosure 245 includes a sound dampening element 256 and is devoid of any gas. The enclosure 245 is completely filled with a liquid 258. Liquid 258 within enclosure 245 may be any liquid selected to alter the propagation speed of the signal 254 as single 254 passes through enclosure 245. In one or more embodiments, liquid 258 is selected to slow the propagation of longitudinal signal 254 through enclosure 245, and may be, for example, water or another viscous fluid or gel. The sound dampening element 256 filters unwanted acoustical signals generated during the calibration process. Sound dampening element 256 may be comprised of foam or any other sound absorbing material. The base 260 of the liquid enclosure 245 is positioned on the first surface 204 of the calibration tool 200 near a calibration plane 262 of the block 202. In some embodiments, the search unit 243 may be equipped with a gasket or other suitable barrier 261 (see FIG. 3A) forming apparatus disposed between the base 260 of the liquid enclosure 245 and the first surface 204 of the calibration tool 200. In one or more embodiments, bores 214a-214e are aligned such that a calibration plane 262 passes through the bores 214 and is oriented perpendicular to the first surface 204 of the block 202.

During the calibration process, the transducer elements 246 generate a longitudinal signal 254 directed at a fixed sound path or half path focus along the calibration plane 262, and passing through the liquid enclosure 245, liquid 258 and the calibration block 202. The transducer elements 246 can be pulsed individually, simultaneously, or in an operator configured order relative to each other to create a desired beam angle or pattern. In the calibration process, preferably the longitudinal signal 254 is generated in a sectorial pattern and at a frequency of between 1.5 MHz and 2.25 MHz, although other patterns and frequencies may be utilized. Longitudinal sound waves 254 are used in lieu of shear sound waves due to the acoustic properties of HDPE in that shear waves have a shorter wave length than longitudinal sound waves 254 and therefore tend to not possess enough energy to propagate through HDPE as effectively as longitudinal sound waves. Due to the difference in elemental composition between the liquid 258 and the calibration block 202, the velocity of the longitudinal signal 254 traveling through the liquid 258 inside the liquid enclosure 245 is slower than the signal 254 velocity traveling through the calibration block 202. The change in elemental composition between the liquid 258 and the calibration block 202 causes the signal the signal 254 to be refracted at the first surface of the block 202, further enhancing wave steeling.

As the signal 254 passes through the first surface 204 of the calibration block 202, the refracted longitudinal signal 254 is directed or swept at a plurality of angles 264. In one or more embodiments, this plurality or range of angles is between approximately 30 and 85 degrees towards the bores 214 on the calibration plane 262, beginning at the first bore 214a and continuing through the depth of the block 212 ending at the furthestmost bore 214, which in the illustrated example is bore 214e.

Figure 2B:
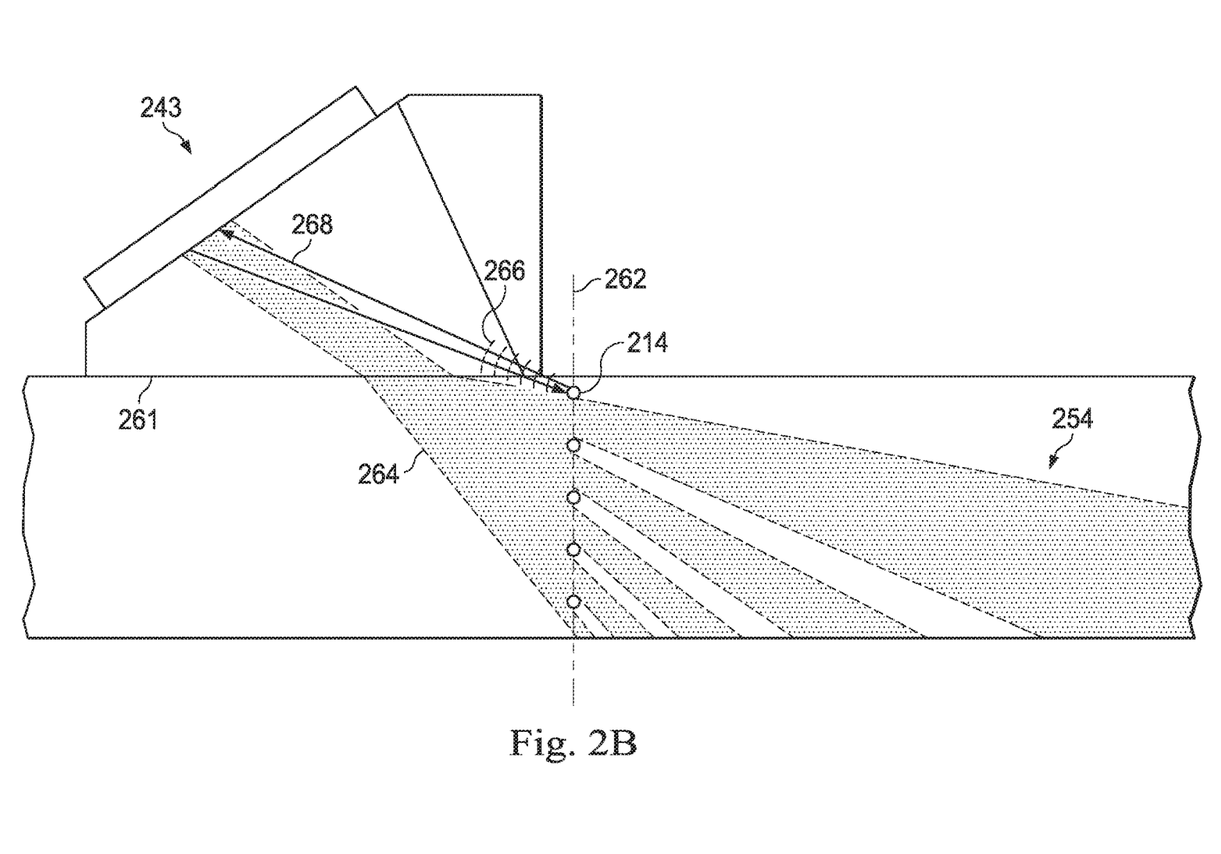
FIG. 2B depicts an elevation view of the calibration process setup using the calibration tool and a search unit during the calibration process, according to one or more illustrative embodiments.

FIG. 2B illustrates an elevation view of the initial calibration arrangement shown in FIG. 2A after a longitudinal signal 254 has been directed at the first bore 214a. Upon encountering a bore 214 in the calibration tool 200 the longitudinal signal 254 is directed back towards the transducer 244 in the form of a reflected signal 266. The combined distance of travel between the longitudinal signal 260 segment and the reflected signal 266 segment is defined as the signal sound path or half-path 268. The transit time of the longitudinal signal 254 and the reflected signal 266 along the sound travel path 268 is defined as the delay time.

Once the reflected signal 266 arrives at the transducer 244, it is converted to an electrical signal which is further processed to recognize the actual time of signal flight and the amplitude (strength) of the signal. At this time an operator can compare the delay time with a calculated time of travel. The calculated time of travel is determined using a plurality of known variables. These variables may include the dimensions of the search unit 243, the distance from the transducer 244 to the first bore 216 and the velocity of longitudinal and reflected signals 254, 266 through the block 202 and the liquid 258 of the liquid enclosure 245. Additionally, an operator may record the strength of the amplitude signal that was converted from the reflected signal 264 from the first bore 214, thus establishing a baseline flaw amplitude signal strength for the calibration tool 200 based upon the known bore depth.

The process of calculating delay and recording amplitude signal strength is repeated for each bore 214a-214e along the calibration plane 262 beginning at the bore 214a nearest to the first bore 214 and ending at the furthermost bore 214e of the block 202. In one or more embodiments, the diameters of the bores 214a-214e within the block 202 are substantially the same so as to ensure that the amplitude signal strength from each bore 214 remains constant. However, as the longitudinal and reflected signals 254, 266 travel along the signal path 266 within the block 202 they become attenuated. To compensate for attenuation through the block 202, the gain for each amplitude signal may be manually and sequentially adjusted for each bore 214 located at different depths along the calibration plane 262, beginning first bore 214a and ending at the furthest most bore 214e based upon the baseline flaw amplitude signal strength established from the first bore 214a. The data obtained during this process is used to develop a time corrected gain (TCG) which normalizes the amplitude signal response from each of the bores 214 of the calibration tool 200. Because the block 202 of the calibration tool 200 is selected to be of the same material type and grade as the first and second HDPE pipe sections 104, 108, the TCG generated from the block 202 may be used to adjust gain for amplitude signals generated by flaws in the fused. HDPE pipe joint 100.

The calibration process may be further verified by using the search unit 243 to repeat the steps described above. After the verification process is completed the delay times and amplitude strength parameters are evaluated by comparing the results of the initial calibration with the results obtained from the search unit 243 in the calibration verification step.

Figure 3A:
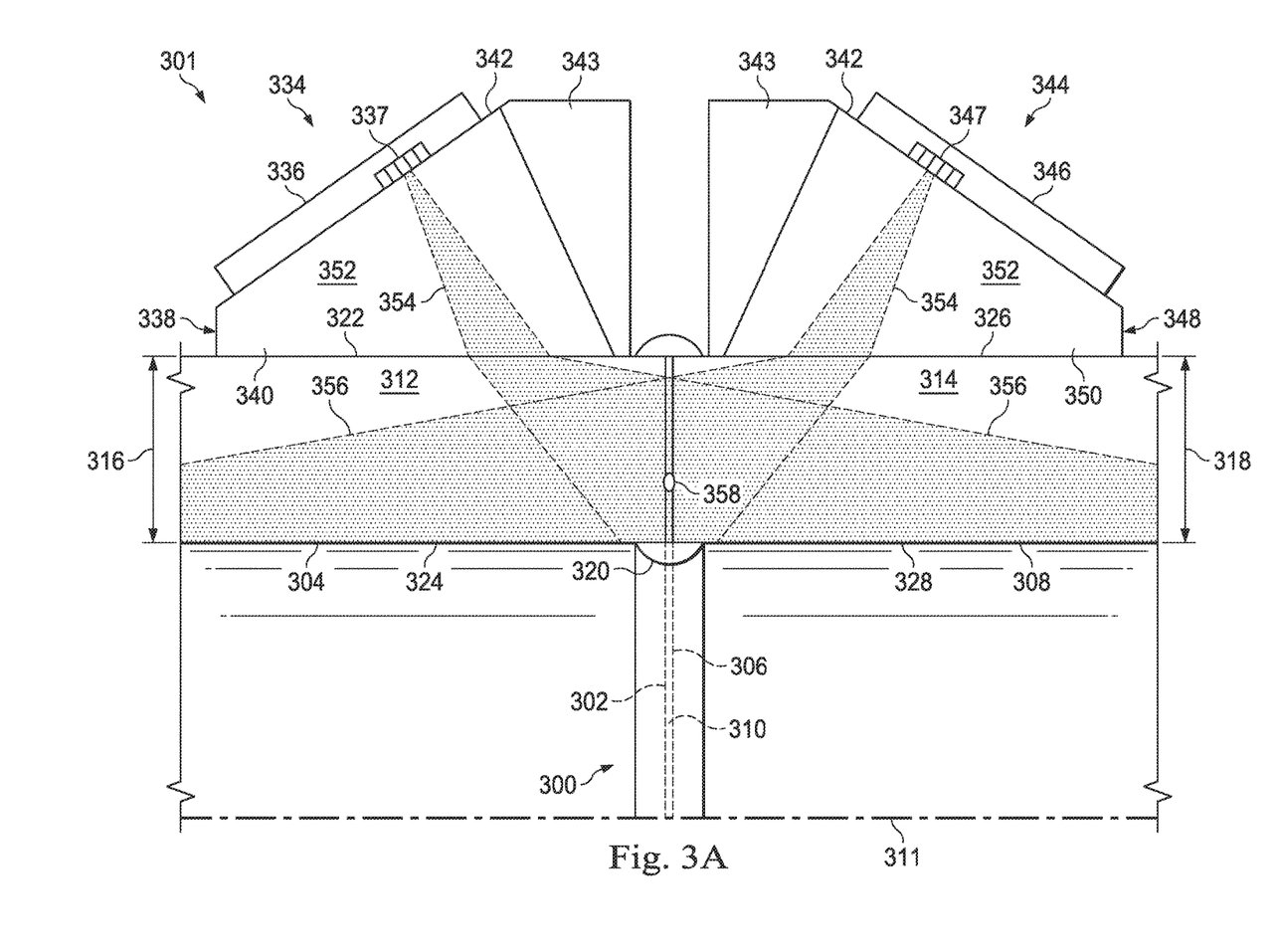
FIG. 3A depicts an enlarged section view of the HDPE pipe inspection tool and fused HDPE pipe joint setup, according to one or more illustrative embodiments.

Referring now to FIGS. 3 and 3A, a fused HDPE pipe joint 300 is illustrated. In FIGS. 3 and 3A, a HDPE pipe inspection tool 301 is positioned adjacent to the pipe joint 300. FIG. 3 illustrates a perspective view while FIG. 3A illustrates an enlarged sectional view of the inspection tool 301 positioned adjacent HDPE pipe joint 300. Illustrated in FIGS. 3 and 3A, is a HDPE pipe joint 300 assembled by fusing the downstream end 302 of a first HDPE pipe section 304 and the upstream end 306 of a second HDPE pipe section 308 together. During the fusion process, a fusion plane 310 perpendicular to the primary axis 311 of the pipe sections 304, 308 and to the outer surfaces 322, 326 of the first HDPE pipe wall 312 and the second HDPE pipe wall 314, respectively, is formed between the two ends 302, 306. The fusion plane 310 has the same length L as the first HDPE pipe wall thickness 316 and the second HDPE pipe wall thickness 318 respectively. During the cooling process, a fusion bead 320 is formed about the fusion plane 310, on the first pipe OD surface 322, the second pipe OD surface 326, and also about the fusion plane 310 on the first pipe II) surface 324 and the second pipe diameter ID surface 328. The fusion bead 320 is typically removed, such as by machining or another finishing process, from the pipe joint 300 after a joint integrity inspection has been performed.

Still referring to FIG. 3A, the HDPE pipe inspection tool 301 includes a first search unit 334 having a first transducer 336 with one or more transducer elements 337 and a first liquid enclosure 338. The first search unit 334 is calibrated using the HDPE calibration tool 200 as previously described. In some embodiments, a plurality of transducer elements 337 may be provided. First transducer 336 may be coupled to a first liquid enclosure 338 having a base surface 340, in which the base surface 340 of the first liquid enclosure 338 is positioned on the OD surface 322 of the first HDPE pipe 304 near the fusion bead 320 of the HDPE pipe joint 300. In a preferred embodiment, first transducer 336 is mounted so that the transducer elements 337 propagate a longitudinal signal 354 at an acute angle relative to primary axis 311 of the pipe sections 304, 308. In this regard, first liquid enclosure 338 may include a sloped surface 342 relative to base surface 340 and to which first transducer 336 is coupled. Additionally, in some embodiments, first liquid enclosure 338 may include a sound dampening element 343 to filter unwanted acoustical signals generated during inspection of the HDPE pipe joint 300. The HDPE pipe inspection tool 301 also includes a second search unit 344 that is positioned adjacent second HDPE pipe section 308, opposite the first search unit 334 across the fusion bead 320 of the HDPE pipe joint 300. Similar to the first search unit 334, the second search unit 344 is also calibrated using the HDPE calibration tool 200. The second search unit 344 has a second transducer 346 with one or more transducer elements 347 and a second liquid enclosure 348. In some embodiments, a plurality of transducer elements 337 may be provided.

The second transducer 346 may be coupled to the second liquid enclosure 348 having a base surface 350, in which the base surface 350 of second liquid enclosure 348 is positioned on the OD surface 326 of the second HDPE pipe 308. In preferred embodiments, the second transducer 346 is mounted so that the transducer elements 347 propagate a longitudinal signal 354 at an acute angle relative to the primary axis 311 of the pipe sections 304, 308. In this regard, the second liquid enclosure 348 may include a sloped surface 342 relative to the base surface 350 and to which the second transducer 346 may be coupled. Similar to the first liquid enclosure 338, the second liquid enclosure 348 may include a sound dampening element 343. The first and second liquid enclosures 338, 348 are preferably devoid of any gas and are completely filled with liquid 352. The transducers 336, 346 may be any transducer capable of generating a longitudinal signal as described herein, such as for example, an Olympus Model 2.25L64-A2 transducer. Likewise the liquid enclosures 338, 348 may be any enclosure suitable for containing a dampening liquid or gel as described herein, such as for example, an Olympus Model ABWX 1663 liquid enclosure. Transducer elements 337, 347 are operable to convert an electric pulse to a longitudinal signal 354 and to convert a returning reflected signal into an electric amplitude signal. In one or more embodiments, due to the acoustic properties of HDPE, a plurality of elements 337, 347 are provided in each of the transducers 336, 346. In some embodiments, five or more elements may be provided in each transducer, while in other embodiments, at least 32 elements may be provided with each transducer. One of the benefits of the system as described herein is that the first and second search units 334, 344 used on the HDPE pipe joint are the of the same configuration and setup as when calibrated. The calibration process is used for confirmation purposes and the overall method requires all variable to remain the same when moving the search units 334, 344 from the calibration tool 200 to the pipe joint 300. Notably, the second search unit 344 is calibrated and verified the same as the first search unit 334 and then put directly on the pipe joint 300. In this regard, the setup for the second search unit 344 will always be identical to the setup for the first search unit 334.

Similar to the process described during the calibration phase, the transducers' elements 337, 347 generate a longitudinal signal 354, such as a sound or pressure wave, directed at a fixed sound path or half path focus along the fusion plane 310 and passing through the liquid enclosures 338, 348, the liquid 352 and the walls of the first and second HDPE pipes 312, 314. The transducer elements 337, 347 can be pulsed individually, simultaneously or in an operator configured arrangement relative to each other to create a desired beam angle or pattern for the longitudinal signal 354. In one or more embodiments of the inspection process, the longitudinal signals 354 may be generated in a sectorial pattern and within a desired frequency range. In one or more embodiments, the frequency range may be between approximately 1.5 MHz and 2.25 MHz. In any case, longitudinal sound wave signals 354 are used in lieu of shear sound wave signals due to the acoustic properties of HDPE. Shear waves have a shorter wave length than longitudinal sound waves 354 and therefore do not tend to possess enough energy to propagate through HDPE material as readily as longitudinal waves. The liquid or gel 352 inside of the liquid enclosures 338, 348 reduces the speed of the signals 354 as they pass through the enclosures 338, 348. This speed reduction facilitates the steering of the signals 354. Additionally, the difference in elemental composition between the liquid 352 and the first and second HDPE pipes 304, 308 causes the wave 354 to be refracted at the OD surfaces 322, 326 of the first and second HDPE pipes 304, 308 respectively enhancing signal steering.

As the signals 354 propagate through OD surfaces 322, 326 of the first and second HDPE pipes 304, 308 the refracted longitudinal signals 354 are directed or swept at a range of angles 356. In one or more preferred embodiments, this range of angles may be swept between approximately 30 to 85 degrees relative to the primary axis 311 of the pipe sections 304, 308 towards the fusion plane 310, beginning at the 01) surfaces 322, 326 of the first and second HDPE pipes sections 304, 308 and terminating at the ID surfaces 324, 328 of the first and second HDPE pipes sections 304, 308 respectively, to detect any fusion flaws 358. Referring to FIG. 3, the first transducer 336 and liquid enclosure 338 (first search unit 334) and the second transducer 346 and liquid enclosure 348 (second search unit 344) are mounted on the first and second HDPE pipe sections 304, 308 using the pipe inspection carriage 360 that fixes the search units 334, 344 relative to one another. In this regard, the first and second search units 334, 344 are positioned at the same distance from the joint 300 as the units 334, 344 were from the calibration plane 262 of the HDPE calibration tool during their respective calibration. The pipe carriage 360 may include a first carriage support 362 and a second carriage support 364 which respectively secure and position the first transducer 336 and liquid enclosure 338 and the second transducer 346 and the liquid enclosure 348 for deployment on HDPE pipes sections 304, 308. Specifically, pipe carriage 360 is movably attached to HDPE pipe sections 304, 308 about the fused HDPE pipe joint 300 so that the first and second search units 334, 344 are opposite one another on either side of the pipe joint 300. The pipe carriage 360 is movable utilizing a mechanism 360a disposed to secure the pipe carriage 360 to a pipe to be inspected and move the carriage circumferentially about the pipe while maintaining the search units in a fixed, spaced apart relationship relative to one another. In this regard, the mechanism may include a skid, track, wheels, chains or similar devices well known in the art for securing and moving an object about a circumferential surface. For example, the mechanism 360a may include a jointed arm or extension 360b that may be placed partially or fully around a pipe, the jointed extension including spaced apart contacts or wheels 360c along the arm 360b to promote rotation. In any event, the mechanism 360a facilitate rotation of the first and second search units 334, 344 about the periphery of the fused HDPE pipe joint 300 while the search units 334, 344 direct longitudinal waves 354 into the joint 300 during the integrity inspection. During the inspection process, a liquid feed 366 line may be provided to convey liquid 352 to the first and second liquid enclosures 338, 348, thus ensuring that the enclosures 338, 348 are devoid of any gas or air gaps. In this regard, liquid 352 from the liquid teed 366 is introduced to the first and liquid enclosures 338, 348 through a first liquid channel 368 and a second liquid channel 370 respectively.

In one or more embodiments, a pulser-receiver module 371 emits a series of electronic pulses to the first and second transducers 336, 346 through a first transducer cable 372 and a second transducer cable 374, respectively. As described further herein, converted signals, i.e., longitudinal signals reflected from a fusion flaw 358 received by the transducers 336, 346 during inspection are relayed to through the first and second transducer cables 372, 374 to a phased array testing instrument (PATI) 376 for display and evaluation. The PATI 376 may be any suitable PATI, such as for example an Olympus Model MX2 PATI.

Figure 3B:
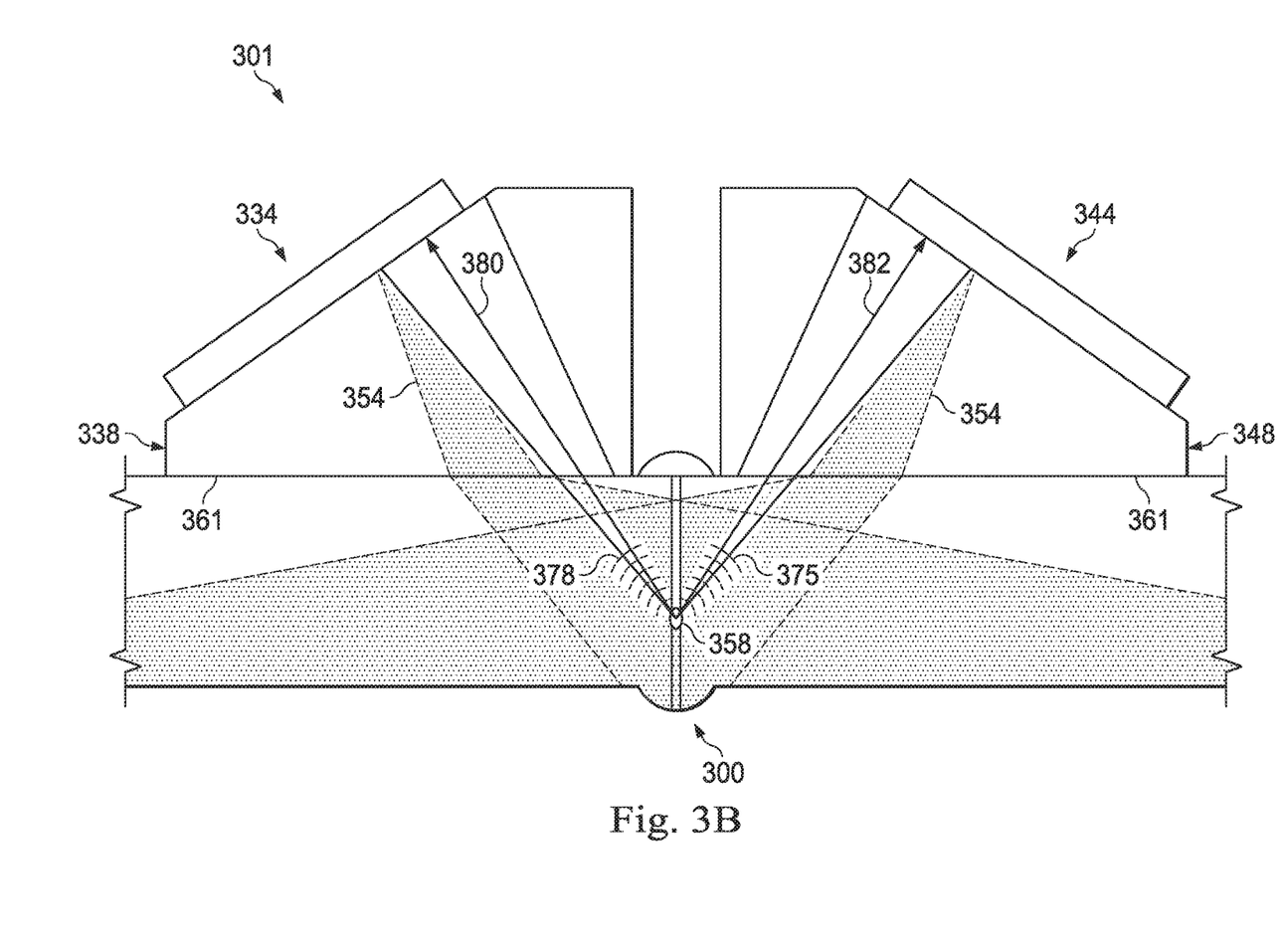
FIG. 3B depicts an enlarged elevation view of the HDPE pipe inspection process setup during the inspection of the fused HDPE pipe joint, according to one or more illustrative embodiments.

Referring to FIG. 3B, an enlarged elevation view of the first and second search units 334, 344 after longitudinal signal 354, such as a longitudinal sound wave, from each transducer 336, 346 has been directed at a fusion flaw 358 within the fused HDPE pipe joint 300 is illustrated. Upon encountering a flaw 358 in the fused HDPE pipe joint 300, the longitudinal signal 354 is directed back towards the transducers 336, 346 in the form of a reflected signal 378. The signal sound path or half-path for the first and second transducer 380, 382 is calculated by combining the time of travel between the longitudinal signal 354 segments and the reflected signal 378 segments for each transducer respectively.

Once the reflected signals 378 arrive at the transducers 336, 346, they are converted to electric signals, i.e., amplitude signals, and relayed to the PATI 376 through the first and second transducer cables 372, 374 respectively for display and operator evaluation. The PATI may include software to add gain to the amplitude signal based upon the TCG developed in the calibration process and the delay time of the signal. Thus, in one or more embodiments, data from the calibration process utilizing the appropriate HDPE calibration tool (selected based on material and grain type) is programmed into the PATI and utilized to adjust the incoming electric signals resulting from the reflected signals 378. Additionally, the PATI may be configured to display the amplitude signals received from the search units 334, 344 on an A-Scan presentation to represent the amplitude signal with respect to time, a B-Scan presentation which depicts a two dimensional image of the amplitude signal plotted as flaw depth or distance with respect to scan distance, a C-Scan presentation which illustrates a two dimensional view of the amplitude signal displayed as a top view of the pipe joint 300 or calibration tool 200 and an S-Scan presentation which represents a two dimensional view of the amplitude signal from a phased array probe corrected for delay and refracted angle.

The B-Scan presentation of the first search unit 334 may then be reviewed for flaw 358 detection. If a signal representing a flaw 358 appears in this presentation, the B-Scan presentation of the second search unit 344 may be reviewed to determine if a similar signal of comparable location (depth) and length is present. If the signal is not seen on the B-Scan presentation of each search unit 334, 344, the process described above may be repeated to determine whether the amplitude signal appears again. If the initial amplitude signal was a false indicator, the likelihood of it appearing during the rescan of the pipe joint 300 is minimal.

Figure 4:
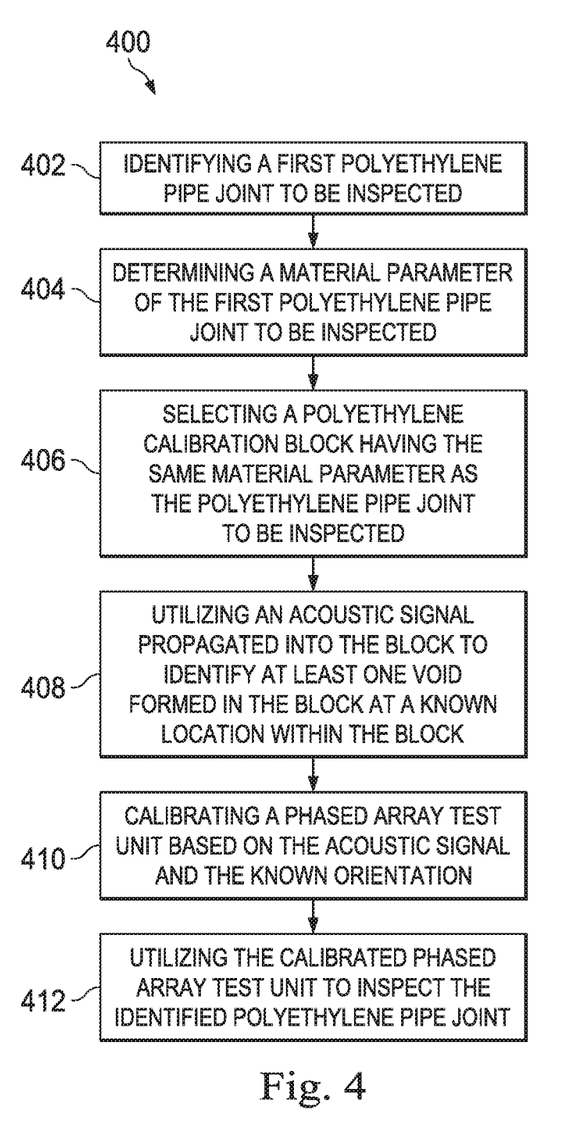
FIG. 4 is a flow chart illustrating a method for inspecting HDPE pipe, according to certain illustrative embodiments of the present disclosure.

With reference to FIG. 4, the pipe inspection operation 400 of the above described systems will be discussed. In step 402 a first HDPE pipe joint 300 to be inspected is identified. The joint 300 is assembled by fusing the end of a first HDPE pipe section 304 to the end of a second HDPE pipe 308. The joint 300 may be newly fused or may be an existing fused joint 300 undergoing maintenance inspection. If the joint 300 is newly fused, the first HDPE pipe OD surface 322 and the second HDPE pipe OD surface 326 are preferably allowed to cool to an ambient temperature prior to inspection. In one or more embodiments, the first HDPE pipe OD surface 322 and the second HDPE pipe OD surface 326 may be prepared by removing any solids. This is particularly true when inspecting an existing joint 300.

Referring now to step 404, the material parameters of the first HDPE pipe joint 300 are identified. The material parameters to be identified may include at least one of the HDPE grade, type and an ASTM material designation code. In some embodiments, at least two or all three of these parameters are identified. Persons of ordinary skill in the art will appreciate that HDPE pipes of the same material parameters are typically used to create a HDPE pipe joint 300. Therefore, verifying these parameters for either first HDPE pipe section 304 or the second HDPE pipe section 308 may ordinarily be sufficient to determine the material parameters of the HDPE pipe joint 300. In step 406, the HDPE calibration block 202 used in the calibration process is selected. A HDPE block 202 is selected by obtaining a block 202 of the same material parameters of the first HDPE pipe 304 or second HDPE pipe 308 as determined in step 404.

Turning now to step 408, once the proper calibration block 202 has been selected, each instrument to be calibrated propagates a series of longitudinal signals 254 along a calibration plane 262 in the block 202 to identify an array of bores 214a-214e formed in the block. The instruments to be calibrated may be the first and second search units 334, 344 as described above. In any event, in one or more embodiments, the bores are of equal size and at known depths on the calibration plane 262. In one or more embodiments, the longitudinal signals are sound waves. Beginning at a bore nearest to the first surface 204 of the block 202, a search unit 243 emits longitudinal signals 254 which are propagated in a sectorial sequence along a half path focus at a refracted angle sweep 262. In one or more embodiments, the sweep range may be between approximately 30 and 85 degrees towards the bores on the calibration plane 262 of the block 202. This process is repeated for each bore through the depth of the block 212 ending at the furthest most bore. It should be noted that the second search unit 344 is configured and calibrated to match that of the first search unit 334. Upon encountering a bore in the block 202, the longitudinal signal 254 is reflected back towards the search unit 243. The reflected signal may be converted into an amplitude signal and may be relayed to a PATI 376 for display. The duration between signal 254 leaving the search unit 243 and the signal returning to the search unit 243 is defined as the signal time of flight distance or sound path distance. The strength of the signal that was reflected from bore nearest to the first surface 204 establishes a baseline flaw amplitude signal strength for the block 202 based upon a known bore depth. The baseline flaw amplitude is established by adjusting the strength of the signal by gain to 80 percent full screen height on the PATI 376 display. Thereafter, the process is repeated for each bore along the calibration plane 262. The baseline flaw amplitude signal strength is compared to the amplitude signal strength received from the remaining bores along the calibration plane 262 and in step 410 adjustments may be made to the amplitude signal by the phased array testing instrument 376 to normalize the amplitude signal strength.

In step 410 the PATI 376 may be calibrated using the array of bores along calibration plane 262 of the block 202. The instrument is calibrated based on the strength of the amplitude signal received from each bore relative to the respective depth of the bore from the first surface 204 within the block 202. The attenuation of the signal 254, 266 through the block 202 requires the addition of gain for each amplitude signal received from a corresponding bore through the depth of the block 212. The data obtained during the calibration process is used to develop a time corrected gain (TCG) which normalizes the amplitude signal response from each of the bores of block 202 and may be programmed in to the PATI 376 for subsequent use during a HDPE pipe inspection. As the block 202 possesses the same material parameters as the pipe joint 300 to be inspected, the TCG generated from the block 202 may be used by the PATI 376 to adjust gain for amplitude signals originating from flaws 358 in the fused HDPE pipe joint 400 as discussed in step 412.

Finally in step 412 the phased array test instrument 376, calibrated using the TCG, may be used to inspect the identified HDPE pipe joint 300. A search unit 334, 344 is positioned on either side of HDPE pipe joint 300 and used to propagate longitudinal inspection signals into the HDPE pipe joint 300. In one or more embodiments, to ensure consistent spacing of the two search units 334, 344, the search units must be rigidly fixed relative to one another on a pipe carriage 360. The pipe carriage 360 supports the first and second search units 334, 344 and is secured to the pipe so as to position the two search units as described about the pipe joint 300. Specifically, the first and second search units 334, 344 are positioned on opposite sides of the pipe joint fusion plane 310. Thereafter the search units are moved in tandem circumferentially about the outer diameter of the pipe sections 304, 308, each propagating a longitudinal signal as described. During inspection, preferably the pipe inspection tool 301 is rotated at least one full revolution around the periphery of the pipe joint 300. As the pipe inspection tool 301 is rotated along the pipe joint, a pulser-receiver module 371 may be used to emit a series of electronic pulses to the first and second search units 334, 344. Each search unit 334, 344 in turn converts the electrical pulses to a longitudinal signals 354 and propagates the signals 354 through the pipe joint 300 towards the fusion plane 310.

The signal 354, upon encountering a flaw 358 in the fusion plane, is reflected as signal 378 back towards the search units 334, 344 from which it was emitted, where the reflected signal may be converted to an electrical signal, and thereafter, may be relayed to the PATI 376. The PATI may be programmed to add gain to the amplitude signal based upon the TCG developed during step 410 and the delay time of the signal. The PATI displays the TCG adjusted amplitude signal on any of a number scan presentation graphs for evaluation. Thus, a pipe inspection tool for inspecting HDPE pipe has been described. Embodiments of the pipe inspection tool may generally include a pipe carriage, a first transducer and a first liquid enclosure containing a liquid, the first transducer abutting the first liquid enclosure and supported on the carriage; a second transducer and a second liquid enclosure containing a liquid, the second transducer abutting the second liquid enclosure and supported on the carriage in a fixed, spaced apart relationship to the first transducer. Other embodiments of a pipe inspection tool may generally include a pipe carriage, a first transducer and a first liquid enclosure containing a liquid, the first transducer abutting the first liquid enclosure and supported on the carriage; a second transducer and a second liquid enclosure containing a liquid, the second transducer abutting the second liquid enclosure and supported on the carriage in a fixed, spaced apart relationship to the first transducer; a pulser-receiver module electronically coupled to the first transducer and the second transducer wherein the first transducer and the second transducer are operable to transmit and receive a longitudinal acoustic signal in response to a pulser signal. Still yet other embodiments of a pipe inspection tool may generally include a pipe carriage, a first transducer and a first liquid enclosure containing a liquid, the first transducer abutting the first liquid enclosure and supported on the carriage; a second transducer and a second liquid enclosure containing a liquid, the second transducer abutting the second liquid enclosure and supported on the carriage in a fixed, spaced apart relationship to the first transducer; a pulser-receiver module electronically coupled to the first transducer and the second transducer wherein the first transducer and the second transducer are operable to transmit and receive a longitudinal acoustic signal in response to a pulser signal; and a phased array testing instrument electrically coupled to the transducers and configured to adjust an amplitude response signal from the transducers based on a time corrected gain curve.

For any of the foregoing embodiments, the pipe inspection tool for inspecting HDPE pipe may include any one of the following elements, alone or in combination with each other:

A liquid enclosure filled with liquid.

A liquid enclosure having a first surface and a second surface formed at an acute angle to one another, wherein the transducer is mounted on the first surface.

Similarly, a pipe inspection calibration tool for calibrating a pipe inspection tool has been described herein. Embodiments of the pipe inspection calibration tool may generally include a block formed of polyethylene of the same material parameters of a pipe joint to be inspected, the block having a first, second, third and fourth surface with two or more spaced apart bores formed in the block, each bore formed along an axis at a known depth relative to and substantially parallel with the first surface.

Likewise, a HDPE pipe inspection apparatus has been described. The HDPE pipe inspection apparatus generally includes a HDPE pipe inspection tool mounted on a HDPE pipe and a pipe inspection calibration tool, the HDPE pipe inspection tool including generally include a pipe carriage movably mounted on a HDPE pipe, a first transducer and a first liquid enclosure containing a liquid, the first transducer abutting the first liquid enclosure and supported on the carriage so that first enclosure is in contact with the pipe; a second transducer and a second liquid enclosure containing a liquid, the second transducer abutting the second liquid enclosure and supported on the carriage in a fixed, spaced apart relationship to the first transducer so that the second enclosure is in contact with the pipe; and the pipe inspection calibration tool generally including a block formed of polyethylene of the same material parameters of a pipe joint to be inspected, the block having a first surface with two or more spaced apart bores formed in the block, each bore formed along an axis at a known depth relative to and substantially parallel with the first surface. Other embodiments of a pipe inspection apparatus may generally include a pipe carriage movably mounted on a HDPE pipe, a first transducer and a first liquid enclosure containing a liquid, the first transducer abutting the first liquid enclosure and supported on the carriage so that first enclosure is in contact with the pipe; a second transducer and a second liquid enclosure containing a liquid, the second transducer abutting the second liquid enclosure and supported on the carriage in a fixed, spaced apart relationship to the first transducer so that second enclosure is in contact with the pipe; a pulser-receiver module electronically coupled to the first transducer and the second transducer wherein the first transducer and the second transducer are operable to transmit and receive a longitudinal acoustic signal in response to a pulser signal; and a pipe inspection calibration tool generally including a block formed of polyethylene of the same material parameters of a pipe joint to be inspected, the block having a first surface with two or more spaced apart bores formed in the block, each bore formed along an axis at a known depth relative to and substantially parallel with the first surface. Still yet other embodiments of a pipe inspection tool may generally include a pipe carriage movably mounted on a HDPE pipe, a first transducer and a first liquid enclosure containing a liquid, the first transducer abutting the first liquid enclosure and supported on the carriage so that first enclosure is in contact with the pipe; a second transducer and a second liquid enclosure containing a liquid, the second transducer abutting the second liquid enclosure and supported on the carriage in a fixed, spaced apart relationship to the first transducer so that second enclosure is in contact with the pipe; a pulser-receiver module electronically coupled to the first transducer and the second transducer wherein the first transducer and the second transducer are operable to transmit and receive a longitudinal acoustic signal in response to a pulser signal; and a phased array testing instrument electrically coupled to the transducers and configured to adjust an amplitude response signal from the transducers based on a time corrected gain curve; and a pipe inspection calibration tool generally including a block formed of polyethylene of the same material parameters of a pipe joint to be inspected, the block having a first surface with two or more spaced apart bores formed in the block, each bore formed along an axis at a known depth relative to and substantially parallel with the first surface.

For any of the foregoing embodiments, the pipe inspection tool for inspecting HDPE pipe may include any one of the following elements, alone or in combination with each other:

A liquid enclosure filled with liquid.

A liquid enclosure having a first surface and a second surface formed at an acute angle to one another, wherein the transducer is mounted on the first surface.

Finally a method for inspecting HDPE pipe has been described herein, where in the method includes identifying a first polyethylene pipe to be inspected, determining a material parameter of the first polyethylene pipe to be inspected, selecting a polyethylene calibration block having the same material parameter as the polyethylene pipe to be inspected, utilizing an acoustic signal propagated into the block to identify at least one void formed in the block at a known location within the block, calibrating a phased array test instrument based on the acoustic signal and the known orientation; and utilizing the calibrated phased array test unit to inspect the identified polyethylene pipe.

For the foregoing embodiments, the method may include any one the following steps, alone or in combination with each other:

Establishing a time corrected gain curve calibrating an amplitude response signal to each void in an array of voids at different depths within the block based on known locations of the voids.

Verifying sound path distance parameters of the calibration block.

Generating an electric signal and converting the electric signal to an acoustic signal and introducing the acoustic signal into the identified high density polyethylene pipe.

Introducing the acoustic signal at a first location on a perimeter about the identified high density polyethylene pipe.

Introducing the acoustical signal at a plurality of spaced apart locations on the perimeter of the identified high density polyethylene pipe.

Introducing the acoustical signal using a transducer positioned adjacent the identified high density polyethylene pipe, Moving the transducer along the perimeter of the identified high density polyethylene pipe.

Moving the transducer through at least 360 degrees of the perimeter.

Converting the electrical signals comprises generating at least two sets of acoustic signals which are introduced simultaneously at spaced apart locations on the perimeter.

Utilizing the calibrated phased array test unit to receive a reflected longitudinal signal and determining a characteristic of the identified high density polyethylene pipe based on the reflected longitudinal signal.

Introducing the acoustic signal by propagating the acoustic signal through a liquid and then into the identified high density polyethylene pipe.

Determining the material parameter of the first high density polyethylene pipe is accomplished by identifying the first high density polyethylene pipe ASTM material designation code.

Selecting a high density polyethylene calibration block further comprises using a calibration block with a grain orientation and thickness that matches the grain orientation and thickness of the identified high density polyethylene pipe.

Utilizing the acoustic signal comprises propagating acoustic signals into the block to identify at least two, spaced apart voids formed in the block at known locations within the block.

Introducing the acoustical signal to the identified high density polyethylene pipe in a sectorial sequence at an acute angle.

Inspecting the high density polyethylene pipe for fused joint integrity.

Inspecting the fused joint of the high density polyethylene pipe for voids formed within the joint.

What is claimed is:

1. A calibration tool for inspecting high density polyethylene pipe, the calibration tool comprising:
a block formed of high density polyethylene, the block having a first surface substantially perpendicular to a second surface, a single column of bores extending from the second surface, the single column of bores including:
a first bore extending from the second surface, the first bore formed along a first axis that is substantially parallel to the first surface and spaced apart from the first surface at a first depth;
a second bore extending from the second surface, the second bore formed along a second axis that is substantially parallel to the first surface and spaced apart from the first surface at a second depth that is different than the first depth;
a third bore extending from the second surface, the third bore formed along a third axis that is substantially parallel to the first surface and spaced apart from the first surface at a third depth that is different than the first and second depths; and
where each of the bores is aligned vertically and centrally to one another such that a calibration plane passes through each of the bores in the single column where the plane is perpendicular to the first surface of the block.

2. The calibration tool of claim 1, wherein the block has a third surface substantially parallel with the second surface and each of the first, second and third bores extend through the block from the second surface to the third surface.

3. The calibration tool of claim 1, wherein the block further comprises a fourth bore extending from the second surface, the fourth bore formed along a fourth axis that is substantially parallel to the first surface and spaced apart from the first surface at a fourth depth that is different than the first, second and third depths; and a fifth bore extending from the second surface, the fifth bore formed along a fifth axis that is substantially parallel to the first surface and spaced apart from the first surface at a fifth depth that is different than the first, second, third and fourth depths.

4. The calibration tool of claim 1, wherein the fourth and fifth bores extend through the block from the second surface to the third surface.

5. The calibration tool of claim 1, wherein the material parameters of the high density polyethylene block matches the material parameters of a high density polyethylene block to be inspected.

6. The calibration tool of claim 1, wherein the distance between each bore in the single column is less than twenty five percent of the total block depth.

7. The calibration tool of claim 1, further comprising a transducer mounted on the first surface and arranged to propagate an acoustic signal through the first surface, and a receiver mounted on the first surface to receive a reflection of the acoustic signal from an axial edge of the each bore in the single column.

* * * * *